United States Patent [19]

Moroni et al.

[11] Patent Number: 5,250,541
[45] Date of Patent: Oct. 5, 1993

[54] KYNURENIC ACID DERIVATIVES, THEIR PREPARATION AND PHARMACEUTICAL COMPOSITIONS CONTAINING THEM

[75] Inventors: Flavio Moroni, Florence; Roberto Pellicciari, Perugia, both of Italy

[73] Assignee: Fidia S.p.A., Abano Terme, Italy

[21] Appl. No.: 828,927

[22] Filed: Feb. 5, 1992

[30] Foreign Application Priority Data

Aug. 11, 1989 [IT] Italy ................. 21512 A/89

[51] Int. Cl.$^5$ ............................................. A01N 43/42
[52] U.S. Cl. ..................................... 514/312; 546/156
[58] Field of Search ................ 546/155, 156; 514/312

[56] References Cited

U.S. PATENT DOCUMENTS 5,114,939  5/1992  Preikorn et al. ................... 546/155

Primary Examiner—C. Warren Ivy
Assistant Examiner—Raymond Covington
Attorney, Agent, or Firm—Griffin Butler Whisenhunt & Kurtossy

[57] ABSTRACT

Kynurenic acid derivatives useful as therapeutic agents in treating neurological disorders, for example, thiokynurenic acid, 7-chloro-thio-kynurenic acid, 7-trifluoromethyl-thiokynurenic acid, 7-methoxy-thiokynurenic acid and 5-fluoro-thiokynurenic acid.

9 Claims, No Drawings

KYNURENIC ACID DERIVATIVES, THEIR PREPARATION AND PHARMACEUTICAL COMPOSITIONS CONTAINING THEM

The present invention refers to kynurenic acid derivatives useful as therapeutic agents, to a process and intermediates for their preparation and to pharmaceutical compositions containing them.

The compounds of the invention have the following general formula I

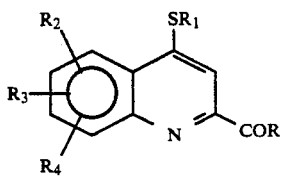

wherein:
R is hydroxy or a physiologically acceptable group which may be converted in vivo to OH group;
$R_1$ is hydrogen or a physiologically acceptable group which may be hydrolized in vivo to give the free thio group;
$R_2$, $R_3$ or $R_4$, which are the same or different, are hydrogen, halogen (chlorine, bromine, iodine or fluorine), $c_1$-$C_6$ alkyl, $C_1$-$C_6$ alkoxy, $C_1$-$C_6$ alkylthio, tririne), fluoromethyl, nitro, cyano, $C_1$-$C_6$ haloalkoxy, $C_1$-$C_6$ alkoxycarbonyl, $C_1$-$C_6$ acyl, hydroxy, $C_1$-$C_6$ acyloxy groups.

Physiologically acceptable groups for R and $R_1$ are widely known and used in medicinal chemistry: typical examples of R groups include ester groups such as methyl, ethyl, t-butyl, pivaloyloxymethyl, t-butoxymethyl and the like and amides.

Examples for $R_1$ groups include alkyl groups such as methyl or ethyl groups, benzyl groups, acyl groups such as acetyl, benzoyl, thyol groups, or even disulfides obtained by oxydation of compounds I themselves, in which case the $R_1$ group has the following formula:

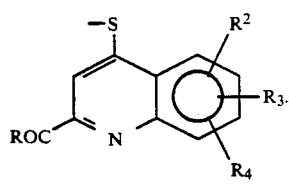

In the compounds of formula I, $C_1$-$C_6$ alkyl preferably means methyl or ethyl; $C_1$-$C_6$ alkoxy is preferably methoxy; $C_1$-$C_6$ acyl is preferably acetyl; $C_1$-$C_6$ alkylthio is preferably methylthio; $C_1$-$C_6$ alkoxycarbonyl is preferably methoxy or ethoxycarbonyl.

Preferred meanings for $R_2$, $R_3$, $R_4$ are hydrogen, chlorine (chlorine, bormine, fluorine or iodine), $c_1$-$C_6$ alkoxy, trifluoromethyl.

Preferred compounds of formula I are those wherein R and $R_1$ are hydrogen, at least one of $R_2$, $R_3$ and $R_4$ is hydrogen and the other two have the above defined meanings; more preferably one of $R_2$, $R_3$, $R_4$ is hydrogen and the other two are independently hydrogen, chlorine, trifluoromethyl or methoxy.

When one or more $R_2$, $R_3$ or $R_4$ group are halogen, they are preferably chlorine in the position 5 and/or 6 and/or 7.

The invention concerns also the pharmaceutically acceptable salts of compounds of formula I with non-toxic acids or bases.

Typical compounds of the invention are:
4-thio-quinoline-2-carboxylic (thiokynurenic) acid
7-chloro-4-thio-quinoline-2-carboxylic acid
7-bromo-4-thio-quinoline-2-carboxylic acid
7-fluoro-4-thio-quinoline-2-carboxylic acid
6-chloro-4-thio-quinoline-2-carboxylic acid
6-bromo-4-thio-quinoline-2-carboxylic acid
6-fluoro-4-thio-quinoline-2-carboxylic acid
5-chloro-4-thio-quinoline-2-carboxylic acid
5,7-dichloro-4-thio-quinoline-2-carboxylic acid
5-chloro-4-thio-quinoline-2-carboxylic acid
7-trifluoromethyl-4-thio-quinoline-2-carboxylic acid
5-chloro-7-trifluoromethyl-4-thio-quinoline-2-carboxylic acid
7-methoxy-5-methyl-4-thio-quinoline-2-carboxylic acid
7-thiomethyl-4-thio-quinoline-2-carboxylic acid
6-chloro-7-thiomethyl-4-thio-quinoline-2-carboxylic acid
5-fluoro-6-chloro-4-thio-quinoline-2-carboxylic acid.

The compounds of the invention are able to counteract some of the effects of glutamate by interacting with the glycine recognition site present in the supramolecular complex known as "NMDA receptor-ion channel complex".

The compounds I may be therefore used in human therapy for the treatment of many neurological disorders due to impaired excitatory glutamatergic transmission. In fact, an excessive presence of glutamate at the synaptic level may cause an abnormal stimulation and finally neuronal death. This death has been defined of excito-toxic type (Olney J. W., Advances in Biochemical Psychopharmac. 27; 375-381; 1981).

The pathology wherein an abnormal functioning of glutamatergic transmission is thought to play an important role is rather wide and it includes extremely different clinical conditions such as Chinese restaurant syndrome, some memory or learning impairments, hepatic coma, some degenerative diseases of CNS such as Huntington's chorea, olivopontocerebellar degeneration, lateral amyotrophic sclerosis, some retinal degenerative conditions and the like. An abnormal stimulation of the glutamate receptors causes also convulsion and is involved in hypoglycemic neuronal damage, lathyrism and neurological disorders connected thereto (amyotrophic lateral sclerosis, Parkinson, dementia) affecting some oceanic populations eating food containing high amounts of aminoacids similar to glycine and glutamate (Science 237; 517-522; 1987).

Another field of the neurological pathology wherein glutamate is almost certainly involved is that of cerebral damages induced by hypoxia or ischemia.

The compounds of the invention, which may be used in the above enormous field of pathology, may be considered derivatives of kynurenic acid, whose presence in low concentration in the brain of different animal species has been recognized as well as its antagonistic activity of the glutamate effect in some classical pharmacological tests such as guinea-pig myenteric plexus (Moroni F. et al, Neuroscience Letters 68, 57-63; 1986; Moroni F. et al, European J. Pharmacol. 163, 123-126; 1989).

It has been shown that the action of kynurenate is mainly due to its interaction with glycine: relatively low concentrations of glycine may in fact antagonise the inhibitory effect of kynurenate. Glycine should be therefore an agonist of a receptor modulating the glutamate activity, whereas kynurenate should be an antagonist of this receptor.

Kynurenic acid derivatives are disclosed in EP-A-0303387 whereas the 2-chloro kynurenic acid has been already studied (Kemp J.A et al. Proc. Natl Acad. Sci Vol. 85 (17), 6547–50, 1988).

The compounds of the invention proved to be endowed with more favourable pharmacological activities then the parent compound. In particular, the compounds I and thiokynurenic acid (R=OH, $R_2$, $R_3$ and $R_4$=H, $R_1$=H) are competitive antagonists of the glycine receptors as shown by the following results:

1) they displace labelled glycine from cortical membranes with an $EC_{50}$ value 5–10 times lower than that of kynurenate;
2) they antagonise in non-competitive way the glutamate effect on NMDA receptors present on guinea-pig ileum: on this test their effect is competitively antagonized by glycine.

The introduction of an halogen atom on the benzene ring of thiokynurenate has enhanced its affinity for the glycine receptors.

The compounds I were also active in mouse cerebral cortex slices according to Proc. Natl. Acad. Sci. USA 85; 6547–6550—1988, in the prevention of glutamate toxicity in cultured cells and in the prevention of NMDA induced convulsions in mice.

In this test the compounds I were from 3 to 50 times more active than the corresponding kynurenic acid derivatives. In particular 7-chloro-4-thiokynurenic acid at a concentration of 0.08 µM antagonises the glutamate neurotoxicity in cultured cells; at the concentration of 1 µM it displaces 50% of labelled glycine from its binding sites in cortical membranes and at a concentration of 5 µM it antagonises 50% of glutamate or NMDA actions on guinea-pig terminal ileum or on brain slices whereas 5,7-dichlorothiokynurenic acid antagonises NMDA induced convulsions in mice at doses of 5–20 mg/kg.

From the above results, it is evident that 4thiokynurenic acid and the derivatives I are competitive antagonists of a particular kind of glycine receptors. They are therefore useful for modulating the aminoacidergic excitatory neuro-transmission, particularly for the treatment of pathological conditions characterized by abnormal stimulation of NMDA receptors, such as:

1) cerebral hypoxic or ischemic syndromes where thiokynurenate could also act as radical scavenger.
2) Convulsions.
3) Hypoglycemia.
4) Cerebral and spinal thrauma.
5) Muscular spasms of central origin.
6) Neurodegenerative diseases (lateral amyotrophic sclerosis, olivopontocerebellar atrophy, ataxis etc.).
7) Cephalgias of different origin (the spreading depression, combined with some forms of cephalgias, is antagonized by NMDA antagonists).
8) Painful syndromes difficult to treat or to diagnose (trigeminus neuralgia, pains due to "ghost limb" etc).
9) Encephalopathy connected with AIDS.
10) Hepatic encephalopathy.
11) Hydrocephalus.
12) Lathyrism and mussels poisoning.
13) Psycho-motor excitement.
14) Insomnia. mania etc.)

For the considered therapeutic use, the compounds I will be formulated in suitable pharmaceutical compositions using conventional excipients and methods.

The compounds may be administered orally or parentally at doses ranging from 0.1 to about 10 g/day.

The compounds of the invention are prepared by a process comprising the reaction of compounds of formula II

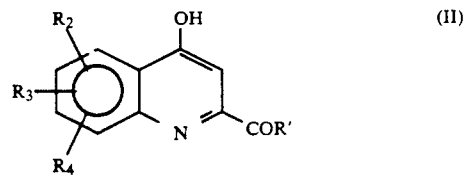

wherein $R_2$, $R_3$ and $R_4$ are as defined above and R' is OH or a group which may be converted in hydroxy group, with N,N-dimethylthiocarbamoyl chloride.

The obtained compounds of formula III

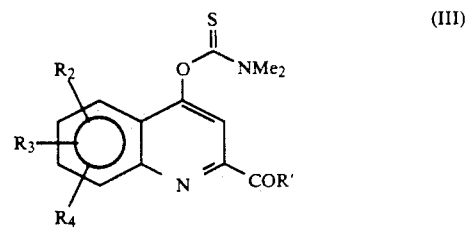

wherein $R_2$, $R_3$, $R_4$ and R' are as above defined, are transformed into compounds IV by treatment with acids

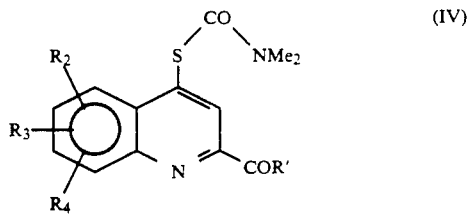

wherein $R_2$, $R_3$, $R_4$ and R' are as above defined, which are transformed into compounds I by hydrolysis and cleavage of the optional protective group.

The compounds I so obtained may be transformed into "pro-drugs" by known methods of alkylation or acylation of thio groups and/or esterification of the carboxy group.

The mild oxidation of compounds I yields the corresponding symmetric disulfides.

The compounds III and IV are new and are included within the scope of the invention as intermediates useful for the preparation of compounds I.

The compounds II are known or they may be prepared according to known methods.

For instance, easily available anilines V

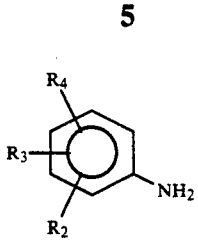

(V)

wherein $R_2$, $R_3$, and $R_4$ are as above defined, are reacted with acetylene dicarboxylate dimethyl ester to give compound II wherein R' is —OCH$_3$.

EXAMPLE 1 a) Kynurenic acid methyl ester

An ether solution of diazomethane (100 ml, 1.5 g) was dropped during 15 min. to a suspension of kynurenic acid (3.0 g, 0.016 mmole) in distilled tetrahydrofuran (200 ml) at 0° C. and under magnetic stirring. Then the reaction mixture is left to warm to room temperature and stirring is continued until complete dissolution of the starting product. Solvent is evaporated off to obtain a crude product which is subjected to flash chromatography on SiO$_2$ (d. 4 cm; h 16 cm) eluting with chloroform (800 ml) and 95:5 chloroform-methanol (800 ml). 2.2 g of the title compound are obtained (73% yield), m.p. 224°-226° C.

$^1$H—NMR (CDCl$_3$+CD$_3$) δ: 3.95 (s, 3H); 7.45 (m, 4H); 8.15 (d, 1H) ppm.

b) N,N-dimethyl-thiocarbamoyl-kynurenic acid methyl ester (III)

A solution of the product from step a) (700 mg, 13.4 mmoles) in distilled dimethylformamide (5 ml), at 25° C. and under magnetic stirring, is added with 1,4-diazabicyclooctane (1.35 g, 12.04 mmoles) and N,N'-dimethyl-thiocarbamoyl chloride (425 mg, 13.4 mmoles). The reaction mixture is stirred until complete disappearing of the starting compound, then it is diluted with water (20 ml) and cooled to $=-5°$ C. The precipitated solid is filtered and dried under vacuum. 900 mg of (IIIb) are obtained (92% yield), m.p. 131.134° C.

$^1$H—NMR (CDCl$^3$)δ: 3.5 (d, 6H); 4.05 (s, 3H); 7.8 (m, 4H); 8.4 (d,1H) ppm.

IR (CDCl$_3$) : 1720, 1530 cm$^{-1}$.

c) N,N-dimethyl-thiolcarbamoyl-kynurenic acid methyl ester (IV)

A solution of (IIIb) (200 mg, 0.70 mmole) in methanol (20 ml), under magnetic stirring, is added with 37% HCl (0.5 ml). The reaction mixture is stirred for 10 min., the solvent is evaporated off under reduced pressure, heating to 40° C. 200 mg of (IVc) are obtained, m.p. 121°-124° C.

$^1$H-NMR (CDCl$_3$)δ: 3.1 (s broad, 6H); 4.05 (s, 3H); 7.8 (m,2H); 8.2 (m, 1H); 8.6 (s, 1H); 9.1 (d, 1H) ppm. IR (CDCl$_3$) 1720, 1680, 1625 cm$^{-1}$.

d) thiokynurenic acid (Id)

(IVc) (2.8 g, 9.0 mmoles) is suspended in 10% NaOH (30 ml) and magnetically stirred for 15 hours at room temperature. The reaction mixture is acidified with 10% HCl to pH=4, then the precipitated solid is filtered and dried under vacuum. 2.1 g of (Id) (100% yield) are obtained, m.p. 230°-233° C. (dec.).

$^1$H—NMR (CD OD) δ: 7.5 (m, 1H); 7.75 (m, 1H); 7.90 (d, 1H); 8.05 (s, 1H); 8.75 (d, 1H) ppm. $^{13}$C-NMR (CD$_3$OD) δ: 121.09, 125.96, 127.16, 129.81, 134.23, 165,51 ppm.

MASS (m/z): 205.6 (M+).

EXAMPLE 2 a) 7-chloro-kynurenic acid methyl ester

A solution of 3-chloroaniline (16.6 ml, 0.15 mole) in methanol (156 ml), under magnetic stirring, is added with a solution of acetylene-dicarboxylate dimethyl ester (19.2 ml, 0.15 mole) in methanol (156 ml). The resulting solution is refluxed for 30 min. Solvent is evaporated off and the residue is taken up into 200 g of diphenyl ether. The solution is refluxed for 15 min., then cooled and diluted with petroleum ether (400 ml). The formed precipitate is filtered, to obtain 37 g of a mixture of 5-chloro- and 7-chloro- kynurenate. This precipitate is heated to 70° C. in 160 g of glacial acetic acid, then, after cooling, the insoluble 7-chloro-kynurenic acid methyl ester is filtered. 26.5 g of the product (72% yield) are obtained upon cooling; m.p. 291°-292° C.

b) 7-chloro-kynurenic acid

The methyl ester from step a) is added to a 10% sodium hydroxide solution (5 ml). The resulting suspension is magnetically stirred at room temperature for 30 min., then washed with ethyl ether (2×3 ml). The aqueous phases are acidified with 10% hydrochloric acid to obtain a precipitate which is filtered and dried, to obtain 0.170 g of the title product (76% yield); m.p. 285°-287° C.

$^1$H—NMR (NaOD) δ: 6.75 (s, 1H, H$_3$); 6.85 (dd, 1H, J$_{6-5}$ =7.5 Hz; J$_{6-8}$=1.5 Hz, H$_6$); 7.22 (d, 1H, J$_{8-6}$ Hz, H$_8$); 7.58 (d, 1H, J$_{5-6}$=7.5 Hz, H$_5$) ppm.

c) 7-chloro-kynurenic acid methyl ester N,N-di-methyl-thione-carbamate

A suspension of the ester from step a) (50 g, 0.21 mole) in anhydrous dimethylformamide is added with DABCO (82.5 g, 0.73 mole), then with N,N-dimethyl-thiocarbamoyl chloride (25.9 g, 0.21 mole). The resulting suspension is magnetically stirred at room temperature for 3 hours, then it is diluted with water (800 ml) to precipitate a white solid which is filtered and dried, to obtain 65 g of the title compound (97% yield). $^1$H-NMR (CDCl$_3$) δ: 3.52 (s, 6H, NMe$_2$); 4.07 (s, 3H, MeO) 7.5 (dd, 1H, J$_{6-5}$=8.5 Hz; J$_{6-8}$=1 Hz, H$_6$); 7.82 (d, 1H, J$_{5-6}$=8.5 Hz, H$_5$); 7.97 (s, 1H, H$_3$); 8.27 (d, 1H, J$_{8-6}$=1 Hz, H$_8$) ppm.

d) 7-chloro-kynurenic acid methyl ester N,N-di-methyl-thiol-carbamate

A suspension of the thionecarbamate (65 g, 0.2 mole) from step c) in methanol (1200 ml) is added with 16.7 ml of 37% hydrochloric acid. The suspension, the colour of which turns to yellow, is magnetically stirred at room temperature for 30 minutes. Then the solid is filtered and dried, solvent is partially evaporated to obtain a second precipitation of a solid which is also filtered and dried, to obtain 64.5 g of the title compound (99% yield).

1H—NMR (CDCl$_3$) δ: 3.11 (bs, 6H, NMe$_2$); 4.06 (s; 3H, MeO) 7.56 (dd, 1H, J$_{6-5}$=7.5 Hz; J$_{6-8}$=1.5 Hz, H$_6$); 8.2 (d, 1H, J$_{5-6}$=7.5 Hz, H$_5$); 8.3 (d, 1H, J$_{8-6}$=1.5 Hz, H$_8$) 8.38 (d, 1H, H$_3$) ppm.

e) 7-chloro-thio-kynurenic acid

Thiol-carbamate from step d) (64.5 g, 0.2 mole) is added to a 10% sodium hydroxide solution. The resulting suspension is magnetically stirred at room temperature for 16 hours, then it is washed with ethyl ether (3×150 ml). The aqueous phases are acidified with 10% hydrochloric acid to precipitate a red-orange solid which is filtered and dried, to obtain 47 g of the title compound (98% yield); m.p. 200°–203° C.

$^1$H-NMR (NaOCD) δ: 7.03 (dd, 1H, $J_{6-5}$=8.5 Hz; $J_{6-8}$=1.5 Hz, $H_6$); 7.43 (d, 1H, $J_{8-6}$=1.5 Hz, $H_8$) 7.7 (d, 1H, $H_3$); 8.15 (d, 1H, $J_{5-6}$=8.5 Hz, $H_5$) ppm.

EXAMPLE 3

According to the same method of Example 2, starting form the suitable anilines, the following compounds were prepared:

| Compound | m.p. | $^1$H-NMR (NaODδ) |
|---|---|---|
| 6-chloro-thiokynurenic acid | 215–217(dec) °C. | 7.28(dd, 1H, $J_{7-8}$=8.5Hz; $J_{7-5}$=1Hz, $H_7$); 7.49(d, 1H, $J_{8-7}$=8.5Hz, $H_8$); 7.61(s, 1H, $H_3$); 8.26(d, 1H, $J_{5-7}$=1)ppm. |
| 7-triflvoromethyl-thiokynurenic acid | 155–157° C. | 7.38(dd, 1H, $J_{6-5}$=9Hz; $J_{6-8}$=1.5Hz, $H_6$); 7.7(s, 1H, $H_3$); 7.8(bs, 1H, $H_8$); 8.36(d, 1H, $J_{5-6}$=9Hz, $H_5$)ppm. |
| 7-methoxy-thiokynurenic acid | 134–137° C. | 3.62(s, 3H, MeO—Ar); 6.88 (bs, 1H, $H_8$); 7.6(s, 1H, $H_3$); 7.76(d, 1H, $J_{5-6}$=9Hz, $H_6$); 8.21(d, 1H, $J_{5-6}$=9Hz, $H_5$)ppm. |
| 8-chloro-thiokynurenic acid | 260–261° C. | 6.71(s, 1H, $H_3$); 6.97(t, 1H, $J_{6-5}$=8.4Hz; $J_{6-7}$=8.4Hz, $H_6$); 7.41(dd, 1H, $J_{7-6}$=8.4Hz; $J_{7-5}$=1.5Hz, $H_7$); 7.78(dd, 1H, $J_{5-6}$=8.4Hz; $J_{5-7}$=1.5Hz, H5)ppm. |
| 5-fluor-thiokynurenic acid | 275–277° C. | 6.53(s, 1H, $H_3$); 6.82(t, 1H, $J_{7-6}$=9Hz; $J_{7-8}$=9Hz, $H_7$); 7.1 (dd, 1H, $J_{8-7}$=9Hz; $J_{8-6}$=2Hz, H8); 7.81(dd, 1H, $J_{6-7}$=9Hz; $J_{6-8}$=2Hz, $H_6$)ppm. |
| 5,7-dichloro-thiokynurenic acid | 210–212° C. | 7.05(d, 1H, $J_{6-8}$=1Hz, $H_6$); 7.38 (d. 1H, $J_{8-6}$=1Hz, H8); 7.75 (s, 1H, $H_3$)ppm. |

We claim:

1. Compounds of formula I

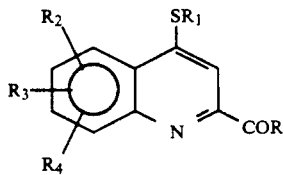

wherein:
R is hydroxy or a physiologically acceptable group which may be converted in vivo to OH group;
$R_1$ is hydrogen or a physiologically acceptable group which may be hydrolized in vivo to give the free thio group;
$R_2$, $R_3$ or $R_4$, which are the same or different, are hydrogen, halogen, $C_1$-$C_6$ alkyl, $C_1$-$C_6$ alkoxy, $C_1$-$C_6$ alkylthio, trifluoromethyl, nitro, cyano, $C_1$-$C_6$ haloalkoxy, $C_1$-$C_6$ alkoxycarbonyl, $C_1$-$C_6$ acyl, hydroxy, $C_1$-$C_6$ acyloxy groups.

2. Compounds according to claim 1 wherein $R_1$ is hydrogen and R is hydroxy.

3. Compounds according to claim 1 wherein $R_2$, $R_3$ and $R_4$ are independently selected from hydrogen, halogen, $C_1$-$C_6$ alkoxy, trifluoromethyl.

4. A compound according to claim 1 selected from thiokynurenic acid 7-chloro-thio-kynurenic acid, 6-chloro-thiokynurenic acid, 7-trifluoromethyl-thiokynurenic acid, 7-methoxy-thiokynurenic acid, 8-chlorothiokynurenic acid, 5-fluoro-thiokynurenic acid, 5,7-dichloro-thiokynurenic acid.

5. Compounds of formula III as intermediates

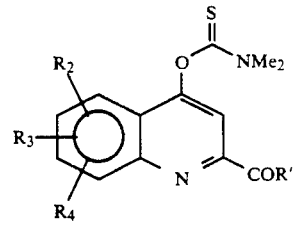

wherein R', $R_2$, $R_3$ and $R_4$ are as defined above.

6. Compounds of formula Iv as intermediates

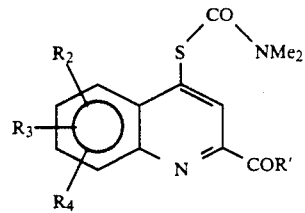

wherein R', $R_2$, $R_3$ and $R_4$ are as defined above.

7. Pharmaceutical compositions containing as the active principle a compound of claim 1 in admixture with a suitable excipient.

8. A composition for the treatment of neurological disorders comprising as an essential ingredient at lest one of the compounds of claim 1.

9. The composition of claim 8 in a daily dosage form of about 0.1 to 10 g.

* * * * *